United States Patent [19]
Kastenhofer

[11] Patent Number: 6,027,477
[45] Date of Patent: *Feb. 22, 2000

[54] CATHETER WITH MULTILAYER TUBE

[75] Inventor: Gerhard Kastenhofer, Effretikon, Switzerland

[73] Assignee: Schneider (Europe) A.G., Bulach, Switzerland

[*] Notice: This patent is subject to a terminal disclaimer.

[21] Appl. No.: 09/053,969

[22] Filed: Apr. 2, 1998

Related U.S. Application Data

[63] Continuation of application No. 08/937,110, Sep. 24, 1997, Pat. No. 5,843,032, which is a continuation of application No. 08/657,004, May 28, 1996, abandoned, which is a continuation of application No. 08/309,234, Sep. 20, 1994, abandoned.

[30] Foreign Application Priority Data

Oct. 27, 1993 [EP] European Pat. Off. .............. 93117403

[51] Int. Cl.[7] .................................................. A61M 29/00
[52] U.S. Cl. .............................................. 604/96; 604/523
[58] Field of Search .............................. 604/96, 280, 264, 604/523; 606/192, 194; 600/433, 435

[56] References Cited

U.S. PATENT DOCUMENTS

| | | | |
|---|---|---|---|
| 3,561,493 | 2/1971 | Maillard | 138/141 |
| 3,618,614 | 11/1971 | Flynn | 128/348 |
| 3,695,921 | 10/1972 | Shepherd et al. | 117/72 |
| 3,814,137 | 6/1974 | Martinez | 138/103 |
| 3,890,976 | 6/1975 | Bazell et al. | 128/351 |
| 4,211,741 | 7/1980 | Ostoich | 264/173 |
| 4,282,876 | 8/1981 | Flynn | 128/349 R |

(List continued on next page.)

FOREIGN PATENT DOCUMENTS

| | | |
|---|---|---|
| 0 277 368 A1 | 8/1988 | European Pat. Off. . |
| 0351687A2 | 1/1990 | European Pat. Off. . |
| 0380102A1 | 8/1990 | European Pat. Off. . |
| 0420488A1 | 4/1991 | European Pat. Off. . |
| 0436501B1 | 7/1991 | European Pat. Off. . |
| 0 452 123 A1 | 10/1991 | European Pat. Off. . |
| 0 520 692 A1 | 12/1992 | European Pat. Off. . |
| 0 279 959 B1 | 8/1993 | European Pat. Off. . |

(List continued on next page.)

*Primary Examiner*—Corrine McDermott
*Assistant Examiner*—Cris L. Rodriguez
*Attorney, Agent, or Firm*—Crompton, Seager & Tufte, LLC

OTHER PUBLICATIONS

European Search Report dated Apr. 14, 1994 in corresponding European Patent Application EP 93117403.1, together with Communication and one page Annex.

Article by Norman G. Gaylord et al., entitled: "Maleation of Linear Low–Density Polyethylene by Reactive Processing"—Gaylord Research Institute, New Providence, New Jersey 07974, pp. 1941–1949.

Article by Norman G. Gaylord, entitled: "Compatibilizing Agents: Structure and Function in Polyblends" J. Macromol. Sci.—Chem., A26 (B), pp. 1211–1229 (1989), Research Institute for Scientists Emeriti, Drew University, Madison, New Jersey 07940.

Brochure dated Feb. 1994 entitled "ASUKA™ 2.9F OTW PTCA Balloon Catheter."

Quantum—PLEXAR® Tie–Layer Resins "The Essential Bond for Coextruded Packaging", 8 pages.

(List continued on next page.)

[57] ABSTRACT

An interventional catheter for angioplasty and the like, comprising a catheter tube formed of two superposed layers of materials different from one another. The inner layer is comprised of a low friction nonkinkable material to avoid risk of clogging of a guide wire in the longitudinal lumen. The outer layer is comprised of a material with higher friction coefficient than the material forming the inner layer. The balloon is welded at its distal end to the outer layer of the catheter tube. The proximal end of the balloon is welded to a tube surrounding the catheter tube.

11 Claims, 1 Drawing Sheet

U.S. PATENT DOCUMENTS

| | | | |
|---|---|---|---|
| 4,323,071 | 4/1982 | Simpson et al. | 128/343 |
| 4,335,723 | 6/1982 | Patel | 128/349 B |
| 4,413,989 | 11/1983 | Schjeldahl et al. | 604/96 |
| 4,596,563 | 6/1986 | Pande | 604/264 |
| 4,597,755 | 7/1986 | Samson et al. | 604/96 |
| 4,627,844 | 12/1986 | Schmitt | 604/264 |
| 4,636,346 | 1/1987 | Gold et al. | 264/139 |
| 4,646,719 | 3/1987 | Neuman et al. | 128/1 D |
| 4,702,252 | 10/1987 | Brooks et al. | 128/344 |
| 4,707,389 | 11/1987 | Ward | 428/36 |
| 4,729,914 | 3/1988 | Kliment et al. | 428/36 |
| 4,744,366 | 5/1988 | Jang | 128/344 |
| 4,762,129 | 8/1988 | Bonzel | 128/344 |
| 4,763,654 | 8/1988 | Jang | 128/344 |
| 4,775,371 | 10/1988 | Mueller, Jr. | 604/280 |
| 4,782,834 | 11/1988 | Maguire et al. | 128/344 |
| 4,820,349 | 4/1989 | Saab | 128/344 |
| 4,900,314 | 2/1990 | Quackenbush | 604/282 |
| 4,906,244 | 3/1990 | Pinchuk et al. | 606/194 |
| 4,921,483 | 5/1990 | Wijay et al. | 604/96 |
| 4,923,450 | 5/1990 | Maeda et al. | 604/265 |
| 4,955,895 | 9/1990 | Sugiyama et al. | 606/194 |
| 4,960,410 | 10/1990 | Pinchuk | 604/96 |
| 4,976,690 | 12/1990 | Solar et al. | 604/96 |
| 4,976,720 | 12/1990 | Machold et al. | 606/194 |
| 4,981,478 | 1/1991 | Evard et al. | 604/282 |
| 4,994,018 | 2/1991 | Saper | 600/18 |
| 4,994,032 | 2/1991 | Sugiyama et al. | 604/96 |
| 4,994,047 | 2/1991 | Walker et al. | 604/264 |
| 5,006,119 | 4/1991 | Acker et al. | 606/27 |
| 5,035,694 | 7/1991 | Kasprzyk et al. | 606/27 |
| 5,041,089 | 8/1991 | Mueller et al. | 604/96 |
| 5,041,100 | 8/1991 | Rowland et al. | 604/265 |
| 5,047,045 | 9/1991 | Arney et al. | 606/194 |
| 5,059,269 | 10/1991 | Hu et al. | 156/244.11 |
| 5,063,018 | 11/1991 | Fontirroche et al. | 264/514 |
| 5,078,727 | 1/1992 | Hannam et al. | 606/194 |
| 5,085,649 | 2/1992 | Flynn | 604/282 |
| 5,100,381 | 3/1992 | Burns | 604/96 |
| 5,100,386 | 3/1992 | Inoue | 604/103 |
| 5,114,423 | 5/1992 | Kasprzyk et al. | 606/27 |
| 5,120,323 | 6/1992 | Shockey et al. | 604/282 |
| 5,195,969 | 3/1993 | Wang et al. | 604/96 |
| 5,195,971 | 3/1993 | Sirhan | 604/96 |
| 5,221,270 | 6/1993 | Parker | 604/282 |
| 5,250,069 | 10/1993 | Nobuyoshi et al. | 606/192 |
| 5,254,090 | 10/1993 | Lombardi et al. | 604/96 |
| 5,267,959 | 12/1993 | Forman | 604/103 |
| 5,270,086 | 12/1993 | Hamlin | 428/35.2 |
| 5,272,012 | 12/1993 | Opolski | 428/423.1 |
| 5,290,230 | 3/1994 | Ainsworth et al. | 604/96 |
| 5,290,306 | 3/1994 | Trotta et al. | 606/194 |
| 5,304,134 | 4/1994 | Kraus | 604/96 |
| 5,338,299 | 8/1994 | Barlow | 604/96 |
| 5,348,536 | 9/1994 | Young et al. | 604/43 |
| 5,356,709 | 10/1994 | Woo et al. | 428/376 |
| 5,383,853 | 1/1995 | Jung et al. | 604/96 |
| 5,397,306 | 3/1995 | Nobuyoshi et al. | 604/96 |
| 5,403,292 | 4/1995 | Ju | 604/282 |
| 5,405,338 | 4/1995 | Kranys | 604/282 |
| 5,409,495 | 4/1995 | Osborn | 606/108 |
| 5,423,754 | 6/1995 | Cornelius et al. | 604/103 |
| 5,425,712 | 6/1995 | Goodin | 604/96 |
| 5,439,454 | 8/1995 | Lo et al. | 604/264 |
| 5,460,608 | 10/1995 | Lodin et al. | 604/96 |
| 5,478,320 | 12/1995 | Trotta | 604/96 |
| 5,499,973 | 3/1996 | Saab | 604/96 |
| 5,501,759 | 3/1996 | Forman | 156/272.8 |
| 5,514,236 | 5/1996 | Avellanet et al. | 156/154 |
| 5,533,985 | 7/1996 | Wang | 604/264 |
| 5,538,510 | 7/1996 | Fontirroche et al. | 604/265 |
| 5,545,151 | 8/1996 | O'Connor et al. | 604/282 |
| 5,549,552 | 8/1996 | Peters et al. | 604/96 |
| 5,558,737 | 9/1996 | Brown et al. | 156/172 |
| 5,562,127 | 10/1996 | Fanselow et al. | 138/137 |
| 5,620,649 | 4/1997 | Trotta | 264/515 |
| 5,676,659 | 10/1997 | McGurk | 604/282 |
| 5,728,063 | 3/1998 | Preissman et al. | 604/96 |
| 5,797,877 | 8/1998 | Hamilton et al. | 604/96 |
| 5,820,594 | 10/1998 | Fontirroche et al. | 604/96 |
| 5,824,173 | 10/1998 | Fontirroche et al. | 156/86 |
| 5,837,313 | 11/1998 | Ding et al. | 427/2.21 |

FOREIGN PATENT DOCUMENTS

| | | |
|---|---|---|
| 0 530 201 B1 | 8/1994 | European Pat. Off. . |
| 0 358 117 B1 | 5/1995 | European Pat. Off. . |
| 0 650 740 A1 | 5/1995 | European Pat. Off. . |
| 0669142A2 | 8/1995 | European Pat. Off. . |
| 2130093A | 5/1984 | United Kingdom . |
| 2209121A | 5/1989 | United Kingdom . |
| WO 89/02763 A1 | 4/1989 | WIPO . |
| 9211893 | 7/1992 | WIPO . |
| WO 93/05842 A1 | 4/1993 | WIPO . |
| WO 95/18647 A2 | 7/1995 | WIPO . |

OTHER PUBLICATIONS

Quantum—PLEXAR® Tie–Layer Resin "Designing PLEXAR® Tie–Layer Resins with Low MVTR Properties", 4 pages (1989).

Quantum—PLEXAR® Tie–Layer Resin "Evaluation of PLEXAR® Tie–Layers for EVOH/PET Coextrusion", 2 pages (1991).

"Physical Constants of Important Polymers", Polymer Handbook, 2nd Edition, A Wiley–Interscience Publication, 1975, p. V–16.

"Physical Constants of Poly(Vinyl Chloride)", Polymer Handbook, 2nd Edition, A Wiley–Interscience Publication, 1975, p. V–41.

"Abrasion & Wear", Encyclopedia of Polymer Science and Engineering, vol. 1, A to Amorphous Polymers, A Wiley-–Interscience Publication, 1985, pp. 15 & 28.

PLEXAR® PX 360 (2 sheets).

PLEXAR® PX 209 (2 sheets).

PLEXAR® Tie–Layer Resins, Products, Applications, and Key Properties (3 sheets).

Quantum Chemical Corporation Material Safety Data Sheet PLEXAR™ (5 sheets).

Chevron Chemical Company Technical Data Sheet Ethylene–Methyl Acrylate Copolymer EMAC SP 2260 (2 sheets).

Chevron Chemical Company Technical Data Sheet Ethylene–Methyl Acrylate Copolymer EMAC SP 2205 (2 sheets).

Bynel® Coextrudable Adhesive Resins Selector Guide (6 sheets).

DuPont Hytrel® Polyester Elastomer Hytrel 7246 (2 sheets).

DSM Engineering Plastic Arnitel®—Available Grades List (4 sheets).

Petrothene® LS 5060–00 (1 sheet).

Petrothene® LM 6007–00 (1 sheet).

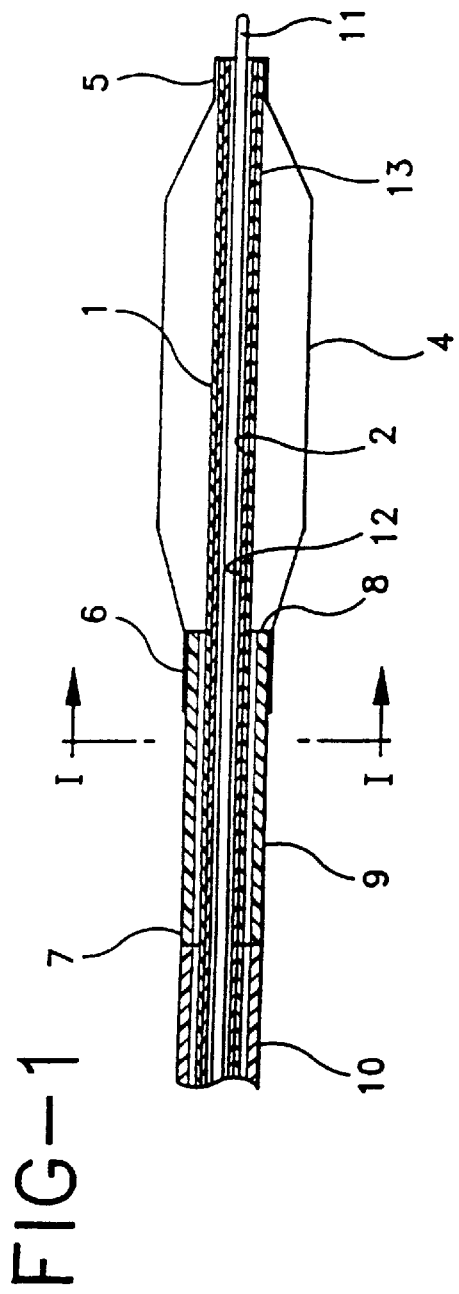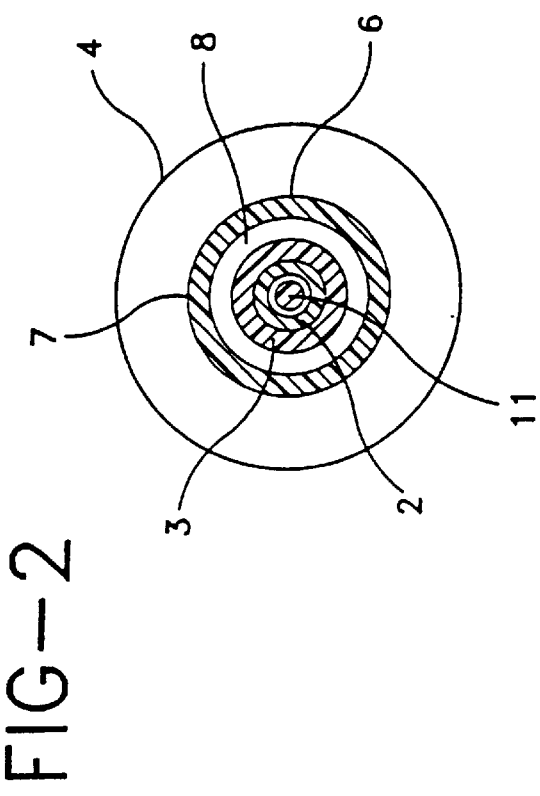

CATHETER WITH MULTILAYER TUBE

This is a continuation of application Ser. No. 08/937,110, filed on Sep. 24, 1997, now Pat. No. 5,843,032 which is a continuation of application Ser. No. 08/657,004, filed on May 28, 1996 (abandoned), which is a continuation of application Ser. No. 08/309,234 filed on Sep. 20, 1994 (abandoned).

BACKGROUND OF THE INVENTION

This invention relates to an interventional catheter comprising a catheter tube having two superposed layers of materials secured in relation to one another and with mechanical properties differing from one another, a longitudinal lumen in said catheter tube for the sliding fit of a guide wire, and a balloon with a proximal end and a distal end, whereby the distal end sealingly surrounds said catheter tube, whereby the catheter tube has an inner layer forming the longitudinal lumen and an outer layer forming the outer surface of the catheter tube.

Over the wire catheters are now widely used for interventions such as percutaneous transluminal angioplasty. A problem with these catheters is that the guide wire may clog into the longitudinal lumen of the catheter; as a result, the guide wire may follow the balloon upon withdrawal thereof after the inflation procedure, thereby making it necessary to re-insert the guide wire into the threaded area of the blood vessel for re-positioning a balloon therein in case a second inflation is needed. Apart of this, the catheter has to achieve an acceptable compromise between the requirements of some stiffness to assure good pushability and of some flexibility to assure kink resistance. In addition, the catheter has to permit safe attachment of the balloon to the catheter tube.

The document WO 92/11893 describes an intra-aortic balloon apparatus comprising a hollow catheter in which is located an elongated member forming a central lumen extending out of the catheter at the distal end thereof. An aortic pumping balloon is positioned over the elongated member; the distal end of the balloon is bonded to a tip affixed to the distal end of the elongated member, and its proximal end is bonded to the distal end of the catheter. In order to achieve a balance of flexibility and remains and to avoid kinking, the elongated member is formed of an inner layer comprised of a soft elastomeric material to impart flexibility to the tubing, and the outer layer is comprised of a hard plastic material to impart structural support to the elongated member. The combination of these two layers is made to achieve a very durable and flexible structure exhibiting a low kink radius. This balloon apparatus cannot be loaded with a guidewire and moved into tortuous vessels with the guidewire loaded inside the elongated tube. The friction between guidewire and the elongated member increases distinctively when the elongated member is shaped into curves. The above procedure would therefore risk that the spiral wound guidewire could be captured in the soft elastomeric plastic material of the inner layer of the elongated member. Although the outer layer of the elongated member that is coextruded onto the inner layer is formed from nylon, a material which is directly weldable to a wide variety of materials, this balloon apparatus cannot be introduced into narrow vessels or narrow stenoses nor can it be passed through narrow punctures to enter the blood vessels. This is because of the relatively large profile of the folded balloon. The large profile is due to the distal fixture of the balloon to the elongated member. The balloon is bonded It) an intermediate tip element which in turn is bonded to the elongated member.

U.S. Pat. No. 4,323,071 describes a combination guiding catheter assembly and dilating catheter assembly. The guiding catheter assembly comprises a first flexible tubular member formed of a material with low coefficient of friction and high flexibility; as this first tubular member is too flexible to serve as a guiding catheter because it could not be properly manipulated in the body of a patient, a second tubular member made of a heat shrinkable tubing is provided to encase the first tubular member. The distal end of this assembly is preshaped to form a shape corresponding to the standard coronary catheter and the proximal end of the assembly is provided with attachment means to provide a leak-proof adhesive-free connection. The Dilating catheter assembly is disposed within the guiding catheter assembly and comprises a first tubular member coaxially disposed within a second tubular member having formed thereon a balloon at its distal end, both these tubular members being made of shrink tubing; an annular flow passage between the first and second tubular members allows introduction of fluid into the balloon for inflation thereof. The proximal end of this assembly is inserted in an adapter body for connection to an appropriate syringe system. A dilator consisting of a flexible plastic tube with a teflon coated guide wire therein is used to position the guiding catheter assembly in the proper location. Within this frame, the guide wire is first inserted conventionally into the blood vessel; the dilator is then positioned in the guiding catheter assembly to straighten it, and the dilator and guiding catheter are passed over the guide wire into the blood vessel; when the guiding catheter is in the proper location, the dilator and guide wire are withdrawn from the guiding catheter and the dilating catheter assembly can be inserted into the guiding catheter assembly, which operation is facilitated be the low coefficient of friction of the first tubular member of the guiding catheter assembly. A small guide wire may be utilized if necessary to precisely position the balloon of the dilating catheter assembly; if so, this small guide wire has to be inserted into the first tubular member of the dilating catheter assembly so that it extends from the distal portion thereof. This guide wire may be removed once the balloon is in the proper location.

This publication shows a catheter shaft made from a composited material that is achieved by heat shrinking. The material for the inner layer of the composite material is selected from materials rendering low friction. Any instrument inserted into a catheter shaft made from this composite material can easily be moved inside the shaft even after the shaft has been bent and is kept in narrow curves. The shaft for the dilation balloon catheter shown in this publication does not use composite material for its construction. It uses conventional material in one single layer. Because the balloon must be welded or otherwise securely bonded to the catheter shaft to withstand the extraordinary high inflation pressures used in angioplasty, the shaft material for this dilatation balloon catheter has to be selected for good bond characteristics and cannot be selected for good friction characteristics. Therefore this catheter still presents the problem that in tortuous vessels, when the catheter shaft has to follow numerous bends of the vessel, the guidewire can be captured in the shaft. This is specifically troublesome since the dilation catheter has to advance much deeper into the branched vessel system than the guiding catheter which in this publication is shown as made from composite material. For a dilatation catheter the length of the friction creating shaft is longer than the shaft of the guiding catheter and additionally the dilatation catheter shaft is exposed to more vessel curves.

SUMMARY OF THE INVENTION

The purpose of the present invention is to present an interventional low profile balloon catheter that can be moved into tortuous vessels with a guidewire inside the catheter without the risk of the guidewire being captured or clogging in the catheter.

To this effect, the interventional catheter according to the invention complies with the definitions given in the claims.

In that way, there is no more risk of having the guide wire clogging in the longitudinal lumen of the catheter tube, in particular upon withdrawal of the balloon. Withdrawal and re-positioning of a balloon for repeated inflation is therefore rapid, safe and precise, because during withdrawal of the balloon the guidewire can be left in place with the tip of the guidewire at the site of the treatment in the vessel system. As the inner layer forming the longitudinal lumen is separated from the balloon by the outer layer, the choice may be made towards materials having the most appropriate friction and kink resistance coefficients, while safe attachment of the balloon may be made at will on an outer layer of the catheter tube which may be chosen without being influenced by the properties of the inner layer.

The inner layer and the outer layer may be congruent in length so that the catheter shaft can be produced in long tubes which are cut into length to form the individual catheter tube.

Where the two layers of the catheter are produced by extruding the outer layer over the inner layer, a specifically reliable catheter tube is formed in a continuous process. To heat shrink the outer layer onto the inner layer would not allow a continuous process because of the presence of an inner core inside the inner layer. This core has to take up the radial pressure during the heat shrinking process and has to be removed after heat shrinking.

The seal between the balloon and the catheter tube may be achieved by welding the balloon material to the outer layer of the catheter tube. This allows the design of balloon catheters that withstand the extraordinary high inflation pressures used in angioplasty so that these catheters also show the low clogging risk and the low profile given by the invention.

In a preferred form of the invention, the inner layer forming the longitudinal lumen of the catheter tube is made of a polyethilene or of a high density polyethylene, both of which assure an extremely low friction coefficient and an appropriate kink resistance coefficient. In another preferred embodiment, the catheter tube will comprise an outer layer made of a polyamid assuring easy welding of the balloon and a good stiffness at that level. These and other objects will become readily apparent from the following detailed description with reference to the accompanying drawings which show, diagrammatically and by way of example only, a preferred embodiment of the invention.

BRIEF DESCRIPTION OF THE DRAWINGS

FIG. 1 is a longitudinal cut out of this embodiment.

FIG. 2 is a section according to line I—I of FIG. 1.

DETAILED DESCRIPTION OF THE INVENTION

The interventional catheter shown in FIGS. 1 and 2 comprises a catheter tube 1 which is formed, in this embodiment, of two superposed continuous layers 2 and 3 extending all over the length of the tube 1; this tubing, which may be achieved by the known co-extrusion technology, i.e. by extruding the outer layer over the inner layer, is comprised of a polyethylene, preferably a high density polyethylene, for the inner layer 2, and of a polyamid for the outer layer 3. The inner layer 2 thus forms a longitudinal lumen 12 with a very low friction coefficient, lower than that of the material forming the outer layer 3, and a non kinking capacity, while the outer layer 3 is easily weldable to the materials commonly used for making balloons for angioplasty and the like.

Over the distal portion of the catheter tube 1 is positioned a balloon 4 the distal end 5 of which is sealed to the outer layer 3 of the catheter tube 1, for instance by welding.

A tube 7 is arranged over the catheter tube 1, at a radial distance thereof, thus defining an inflating lumen 8 for the balloon 4. The proximal end 6 of the balloon 4 is welded onto the distal end of said tube 7.

The tube 7 is exemplified here as being made of two tubes 9 and 10 longitudinally affixed to one another. Preferably the tubes 9 and 10 shall be made of a polyamid to achieve easy fixing by welding procedures and to obtain a stepped stiffness. The proximal end of tube 10 is connected to conventional fittings (not shown) to feed the balloon and drive the catheter assembly. Inside the catheter tube 1 is placed a guide wire 11 in sliding fit within the inner layer 2 forming the longitudinal lumen 12.

As a variant, the two tubes configuration of the tube 7 may be replaced by a single tube or by a configuration having more than two longitudinally affixed tubes.

I claim:

1. An interventional balloon catheter comprising a catheter tube having two superposed layers of materials secured in relation to one another and with mechanical properties differing from one another, a longitudinal lumen in said catheter tube configured to slidably accept a guide wire, and a balloon comprising a balloon material with a proximal end and a distal end, wherein the distal end of the balloon sealingly surrounds the catheter tube, wherein the catheter tube has an inner layer comprising a first material forming the longitudinal lumen and an outer layer comprising a second material forming an outer surface of the catheter tube, wherein the first material has a lower friction coefficient than the second material and wherein the second material is easily weldable to the balloon material.

2. An interventional catheter according to claim 1, wherein the inner layer and the balloon are separated by the outer layer.

3. An interventional catheter according to claim 1, wherein the inner layer and the outer layer are congruent in length.

4. An interventional catheter according to claim 1, wherein the two layers of the catheter tube are produced by extruding the outer layer over the inner layer.

5. An interventional catheter according to claim 1, wherein the seal between the balloon and the catheter tube is achieved by welding the balloon material to the outer layer of the catheter tube.

6. An interventional catheter according to claim 1, wherein the inner layer forming the longitudinal lumen of the catheter tube comprises polyethylene.

7. An interventional catheter according to claim 1, wherein the inner layer forming the longitudinal lumen of the catheter tube comprises high density polyethylene.

8. An interventional catheter according to claim 1, wherein the outer layer comprises polyamid.

9. An interventional catheter comprising a catheter tube having two superposed layers of materials secured in relation to one another and with mechanical properties differing from one another, a longitudinal lumen in said catheter tube for the sliding fit of a guide wire, and a balloon with a proximal end and a distal end, whereby the distal end sealingly surrounds said catheter tube, whereby the catheter tube has an inner layer forming the longitudinal lumen and an outer layer forming the outer surface of the catheter tube, and the inner layer is formed of a material with a lower friction coefficient than the material forming the outer layer, wherein the inner layer forming the longitudinal lumen of the catheter tube is polyethylene, wherein the outer layer is made of polyamide, and the distal end of the balloon is welded to the outer polyamide layer of the catheter tube.

10. An interventional catheter according to claim 9, wherein the two layers of the catheter tube are produced by extruding the outer layer over the inner layer.

11. An interventional catheter according to claim 9, wherein the inner layer forming the longitudinal lumen of the catheter tube is high density polyethylene.

* * * * *

UNITED STATES PATENT AND TRADEMARK OFFICE
Certificate

Patent No. 6,027,477                                                  Patented: February 22, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gerhard Kastenhofer, Bulach, Switzerland; Christine M. Byam, Eden Prarie, MN; and Richard Goodin, Blaine, MN.

Signed and Sealed this Twenty-third Day of March 2004.

<div align="right">

BRIAN L. CASLER
*Supervisory Patent Examiner*
Art Unit 3763

</div>